United States Patent
Iwase et al.

(10) Patent No.: US 9,004,685 B2
(45) Date of Patent: Apr. 14, 2015

(54) IMAGE PROCESSING APPARATUS AND METHOD THEREOF

(71) Applicant: Canon Kabushiki Kaisha, Tokyo (JP)

(72) Inventors: Yoshihiko Iwase, Kyoto (JP); Makoto Sato, Tokyo (JP); Akihito Uji, Kyoto (JP); Nagahisa Yoshimura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/771,441

(22) Filed: Feb. 20, 2013

(65) Prior Publication Data

US 2013/0265543 A1 Oct. 10, 2013

(30) Foreign Application Priority Data

Apr. 4, 2012 (JP) ................................. 2012-085896

(51) Int. Cl.
*A61B 3/14* (2006.01)
*A61B 3/00* (2006.01)
*A61B 3/10* (2006.01)
*A61B 5/00* (2006.01)
*G01B 9/02* (2006.01)
*G01N 21/47* (2006.01)

(52) U.S. Cl.
CPC ............... *A61B 3/102* (2013.01); *A61B 5/0066* (2013.01); *G01B 9/0203* (2013.01); *G01B 9/02082* (2013.01); *G01B 9/02083* (2013.01); *G01B 9/02091* (2013.01); *G01N 21/4795* (2013.01)

(58) Field of Classification Search
USPC ................................................. 351/200–246
See application file for complete search history.

(56) References Cited

U.S. PATENT DOCUMENTS

| | | |
|---|---|---|
| 8,356,898 B2 * | 1/2013 | Ono .............................. 351/206 |
| 8,442,286 B2 | 5/2013 | Imamura et al. |
| 2008/0074617 A1 | 3/2008 | Podoleanu |
| 2010/0202677 A1 | 8/2010 | Imamura et al. |
| 2011/0134392 A1 | 6/2011 | Iwase et al. |
| 2011/0137157 A1 * | 6/2011 | Imamura et al. .............. 600/425 |
| 2011/0211057 A1 | 9/2011 | Iwase et al. |
| 2012/0044457 A1 | 2/2012 | Sato et al. |
| 2012/0057127 A1 | 3/2012 | Iwase et al. |
| 2012/0070049 A1 | 3/2012 | Iwase et al. |
| 2012/0075640 A1 | 3/2012 | Sakagawa et al. |
| 2012/0133950 A1 | 5/2012 | Suehira et al. |

(Continued)

FOREIGN PATENT DOCUMENTS

| | | |
|---|---|---|
| CN | 102186407 A | 9/2011 |
| JP | 2011-030626 A | 2/2011 |

(Continued)

OTHER PUBLICATIONS

Erich Götzinger, et al., "Retinal pigment epithelium segmentation by polarization sensitive optical coherence tomography", Optics Express, vol. 16, No. 21, Oct. 15, 2008, pp. 16410-16422.

(Continued)

*Primary Examiner* — Mohammed Hasan
(74) *Attorney, Agent, or Firm* — Fitzpatrick, Cella, Harper & Scinto

(57) ABSTRACT

An image processing apparatus acquires a tomographic image of an eye to be examined. The image processing apparatus quantifies a distortion in a region determined from the tomographic image. The region includes a photoreceptor layer or a retinal pigment epithelium.

36 Claims, 14 Drawing Sheets

(56) References Cited

U.S. PATENT DOCUMENTS

2012/0218515 A1* 8/2012 Imamura .................. 351/206
2012/0288175 A1 11/2012 Iwase et al.
2013/0272590 A1 10/2013 Imamura et al.
2014/0085606 A1* 3/2014 Miyasa et al. ............ 351/206

FOREIGN PATENT DOCUMENTS

WO 2011/022488 A2 2/2011
WO 2012/068408 A1 5/2012

OTHER PUBLICATIONS

Akihito Uji, et al., "New Quantitative Image Analysis Method for Outer Layer of Retina Using OCT", vol. 116, Extra Edition of Journal of Japanese Ophthalmological Society, Japanese Ophthalmological Society, 02-165, Kyoto University, Mar. 1, 2012, p. 280.

Jul. 30, 2013 European Search Report in European Patent Appln. No. 13159353.5.

Sep. 26, 2014 Chinese Official Action in Chinese Patent Appln. No. 201310119869.3.

* cited by examiner

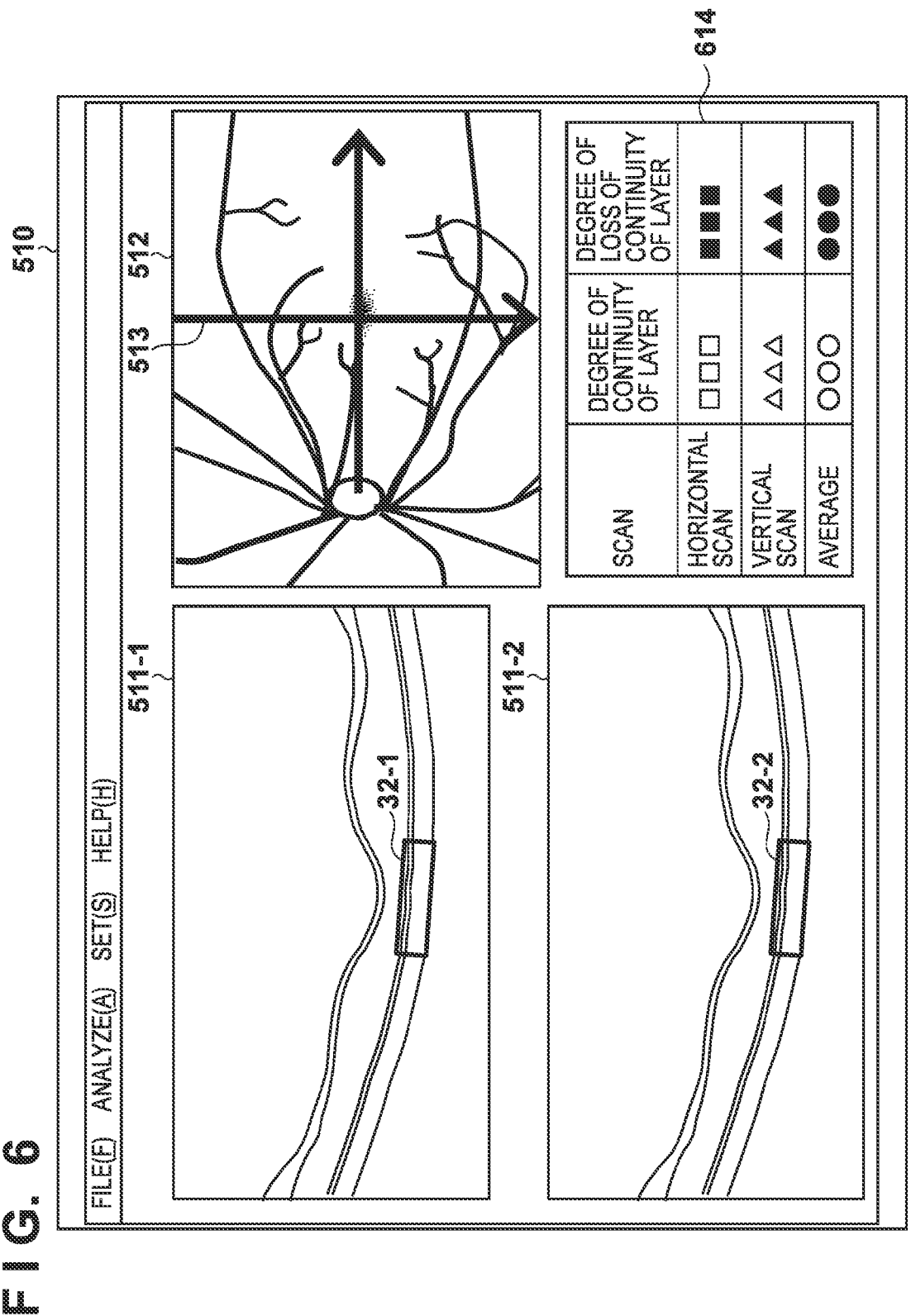

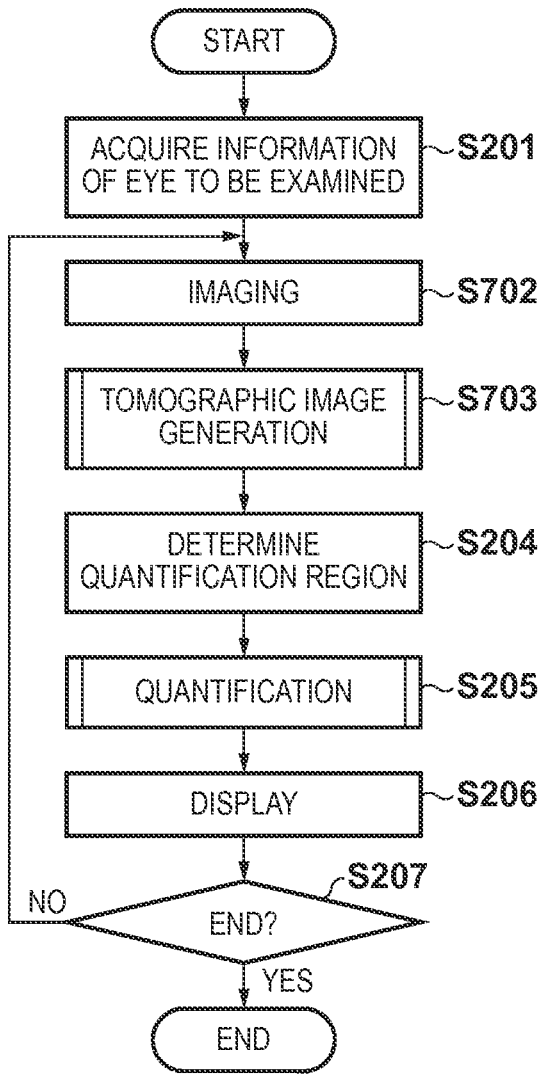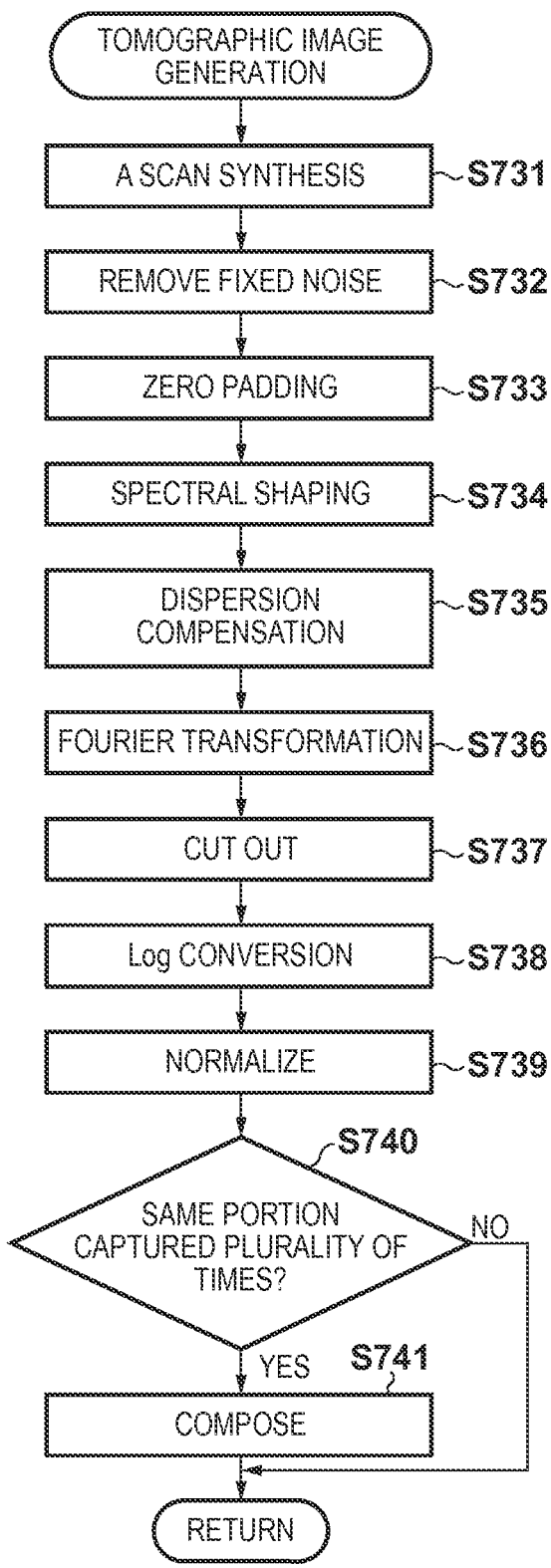

FIG. 11A
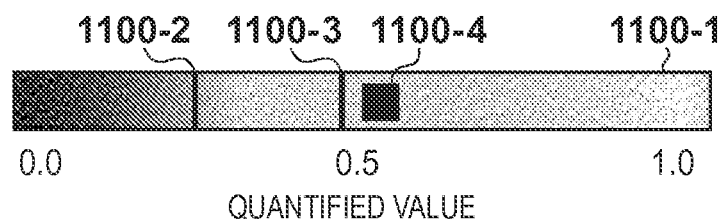
FIG. 11B
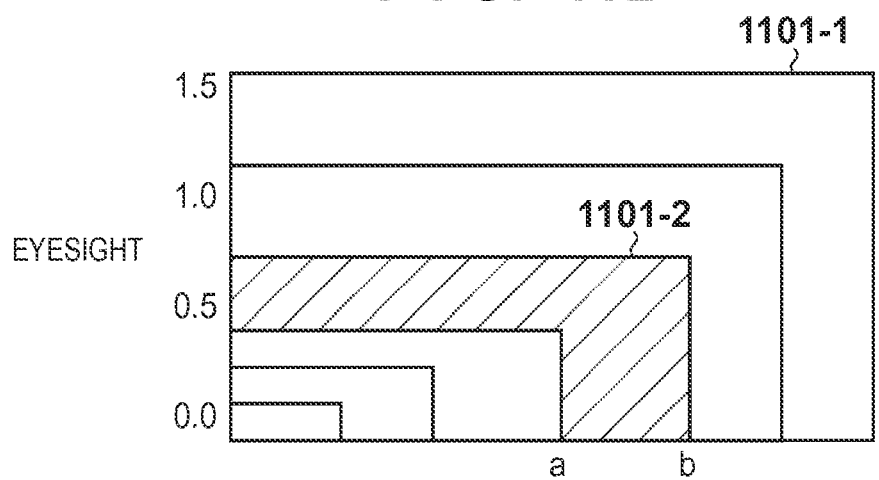
FIG. 11C
| QUANTIFIED VALUE | □□□ |
|---|---|
| EYESIGHT ESTIMATED FROM QUANTIFIED VALUE | △△~×× |
| EYESIGHT IN EYESIGHT TEST | ○○○ |

# IMAGE PROCESSING APPARATUS AND METHOD THEREOF

BACKGROUND OF THE INVENTION

1. Field of the Invention

The present invention relates to an image processing apparatus for processing a tomographic image of an eye to be examined and a method thereof.

2. Description of the Related Art

A tomography imaging apparatus such as an OCT (Optical Coherence Tomography) for an eye can three-dimensionally observe the internal state of a retinal layer. The tomography imaging apparatus has recently received a great deal of attention because of its usefulness in more properly diagnosing diseases. An example of the form of OCT is a TD-OCT (Time Domain OCT) that combines a wideband light source and a Michelson interferometer. The TD-OCT is configured to scan the delay of a reference arm to measure the interference light with the backscattered light of a signal arm, thereby obtaining information of depth resolution. However, it is difficult to quickly acquire an image by the TD-OCT. As a method of acquiring an image at a higher speed, an SD-OCT (Spectral Domain OCT) is known, which uses a wideband light source and acquires an interferogram by a spectroscope. Also known is an SS-OCT (Swept Source OCT) that employs a technique of measuring spectral interference by a single-channel photodetector using a high-speed wavelength swept light source as a light source. In addition, as a functional OCT, a PS-OCT (Polarization Sensitive OCT) is known, which performs imaging using a polarization parameter (retardation and orientation) as one optical characteristic of the tissues of the fundus of an eye.

If a shape change of a retina can be measured in tomographic images captured by the above-described OCTs, the degree of progression of a disease such as glaucoma, age-rated macular degeneration, or diabetic macular edema and the degree of recovery after treatment can quantitatively be diagnosed. To quantitatively measure the shape change of a retina, Japanese Patent Laid-Open No. 2011-030626 (to be referred to as literature 1 hereinafter) discloses a technique of analyzing the degree of unevenness of a retinal layer in age-rated macular degeneration using a computer.

In literature 1, the difference in thickness between a retinal layer obtained by analysis and an estimated normal retinal layer is evaluated. In diabetic macular edema, when a retina swells due to edema, the eyesight gets worse. Hence, treatment is given to decrease the retinal thickness, and the effect of treatment is confirmed using the OCT. In fact, a distortion in the layer structure of the retinal layer, particularly, a change in a photoreceptor layer affects visual performance more than the retinal thickness. Conventionally, a person observes images and judges the degree of distortion in a retinal layer based on his/her experiences. This poses a problem from the viewpoint of objectivity.

SUMMARY OF THE INVENTION

The present invention has been made in consideration of the above-described problem, and has as its object to provide a standard to appropriately evaluate a distortion in a photoreceptor layer.

According to one aspect of the present invention, there is provided image processing apparatus comprising: an acquisition unit configured to acquire a tomographic image of an eye to be examined; and a quantification unit configured to quantify a distortion in a photoreceptor layer in the tomographic image.

According to another aspect of the present invention, there is provided an image processing apparatus comprising: an acquisition unit configured to acquire a tomographic image of an eye to be examined; a detection unit configured to detect a retinal pigment epithelium in the tomographic image; a determination unit configured to determine a region including the retinal pigment epithelium in the tomographic image; and a quantification unit configured to quantify a distortion in a layer included in the region.

According to another aspect of the present invention, there is provided an image processing method comprising steps of: acquiring a tomographic image of an eye to be examined; and quantifying a distortion in a photoreceptor layer in the tomographic image.

Furthermore, according to another aspect of the present invention, there is provided an image processing method comprising steps of: acquiring a tomographic image of an eye to be examined; detecting a retinal pigment epithelium in the tomographic image; determining a region including the retinal pigment epithelium in the tomographic image; and quantifying a distortion in a layer included in the region.

According to the present invention, it is possible to provide a standard to appropriately evaluate a distortion in a photoreceptor layer.

Further features of the present invention will become apparent from the following description of exemplary embodiments with reference to the attached drawings.

BRIEF DESCRIPTION OF THE DRAWINGS

FIG. 6 is a view showing another example of analysis result display;

FIGS. 7A and 7B are flowcharts showing processing of an image processing system according to the fourth embodiment;

FIGS. 11A to 11C are views showing examples of quantified value display;

DESCRIPTION OF THE EMBODIMENTS

An image processing apparatus according to this embodiment is characterized by quantifying a distortion in a photoreceptor layer. This allows provision of a standard to appropriately evaluate a distortion in a photoreceptor layer. Note that "a distortion in a photoreceptor layer" can also be called, for example, "a degree of breakage of a photoreceptor layer itself".

One of methods of quantifying "a distortion in a photoreceptor layer" is a method of obtaining a variation (distribution) in the depth-direction position of a photoreceptor layer (in intermittent layers). More specifically, this is a method of obtaining the "parallelness" of a photoreceptor layer. This method will be described in detail in the first embodiment. Note that the "parallelness" can also be called "orientation".

Another one of the methods of quantifying "a distortion in a photoreceptor layer" is a method of obtaining the intermittence (discontinuity) of a photoreceptor layer. More specifically, this is a method of obtaining the "complexity" and "lacunarity" of a photoreceptor layer. This method will be described in detail in the second embodiment.

Still another one of the methods of quantifying "a distortion in a photoreceptor layer" is a method of obtaining values concerning both the variation and the intermittence. More specifically, this is a method of obtaining the degree of continuity and the degree of loss of continuity of a photoreceptor layer in a plurality of directions. This method will be described in detail in the third embodiment.

First Embodiment

Orientation (Parallelness)

The first embodiment of the present invention will be described below with reference to the accompanying drawings. Note that an image processing system including an image processing apparatus according to this embodiment quantifies the degree of distortion in the layer structure of a retina. In particular, the image processing system quantifies the degree of distortion in a photoreceptor layer near the fovea. Details of the image processing system including the image processing apparatus according to this embodiment will be described below.

Figure 1:
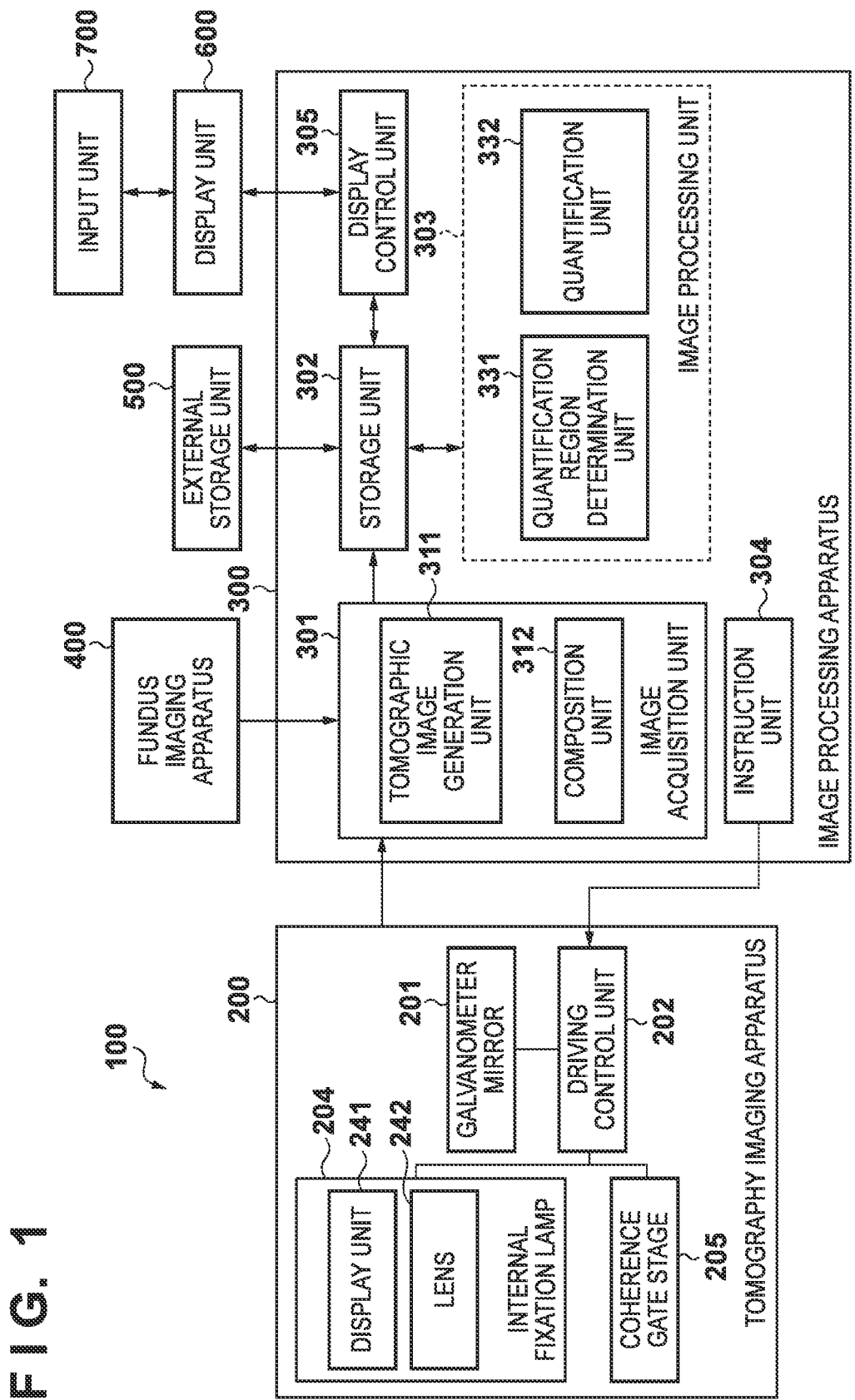
FIG. 1 is a block diagram showing the arrangement of an image processing system according to the first embodiment.

FIG. 1 is a block diagram showing the arrangement of an image processing system 100 including an image processing apparatus 300 according to this embodiment. As shown in FIG. 1, the image processing system 100 is constructed by connecting the image processing apparatus 300 to a tomography imaging apparatus (also referred to as an OCT) 200, a fundus imaging apparatus 400, an external storage unit 500, a display unit 600, and an input unit 700 via an interface.

The tomography imaging apparatus 200 is an apparatus that captures a tomographic image of an eye portion. The device used in the tomography imaging apparatus is, for example, an SD-OCT or SS-OCT. Note that the tomography imaging apparatus 200 is a known apparatus, and a detailed description thereof will be omitted. The tomographic image capture range and the parameters of an internal fixation lamp 204, which are set in accordance with instructions from the image processing apparatus 300, will be explained here.

Referring to FIG. 1, a galvanometer mirror 201 is used to scan measurement light on a fundus, and defines the fundus capture range of the OCT. A driving control unit 202 controls the driving range and speed of the galvanometer mirror 201, thereby defining the capture range in the planar direction and the number of scan lines (the scanning speed in the planar direction) on the fundus. The galvanometer mirror 201 includes two mirrors for X scanning and Y scanning and can scan measurement light within a desired range on the fundus.

The internal fixation lamp 204 includes a display unit 241 and a lens 242. A device formed by arranging a plurality of light-emitting diodes (LEDs) in a matrix is used as the display unit 241. The on positions of the light-emitting diodes are changed in accordance with the part to be captured under the control of the driving control unit 202. Light from the display unit 241 is guided, through the lens 242, to the eye to be examined. The display unit 241 emits 520-nm light, and a desired pattern is displayed by the driving control unit 202.

A coherence gate stage 205 is controlled by the driving control unit 202 to cope with, for example, a difference in the axial length of the eye. The coherence gate represents the position where the optical path of measurement light equals that of reference light in the OCT. In addition, the position of the coherence gate is controlled to control the imaging method, that is, whether to perform imaging on the retinal layer side or enhanced depth imaging (to be referred to as EDI hereinafter) on the side deeper than the retinal layer. If imaging is performed by EDI, the position of the coherence gate is set on the deep side of the retinal layer. For this reason, the chorioidea or RPE can be captured at a high luminance.

The fundus imaging apparatus 400 captures a fundus image of the eye portion. For example, a fundus camera or an SLO (Scanning Laser Ophthalmoscope) is usable as this apparatus.

The image processing apparatus 300 includes an image acquisition unit 301, a storage unit 302, an image processing unit 303, an instruction unit 304, and a display control unit 305. The image acquisition unit 301 includes a tomographic image generation unit 311 and a composition unit 312. The image acquisition unit 301 acquires the signal data of a tomographic image captured by the tomography imaging apparatus 200, performs signal processing to generate a tomographic image, performs composition processing of the generated tomographic image, and stores the generated tomographic image in the storage unit 302. The image processing unit 303 includes a quantification region determination unit 331 and a quantification unit 332. The quantification region determination unit 331 determines a region to quantify the degree of distortion in a photoreceptor layer. The quantification unit 332 quantifies the degree of distortion in the photoreceptor layer in the region determined by the quantification region determination unit 331. The instruction unit 304 instructs imaging parameters and the like for the tomography imaging apparatus 200.

Figure 2A:
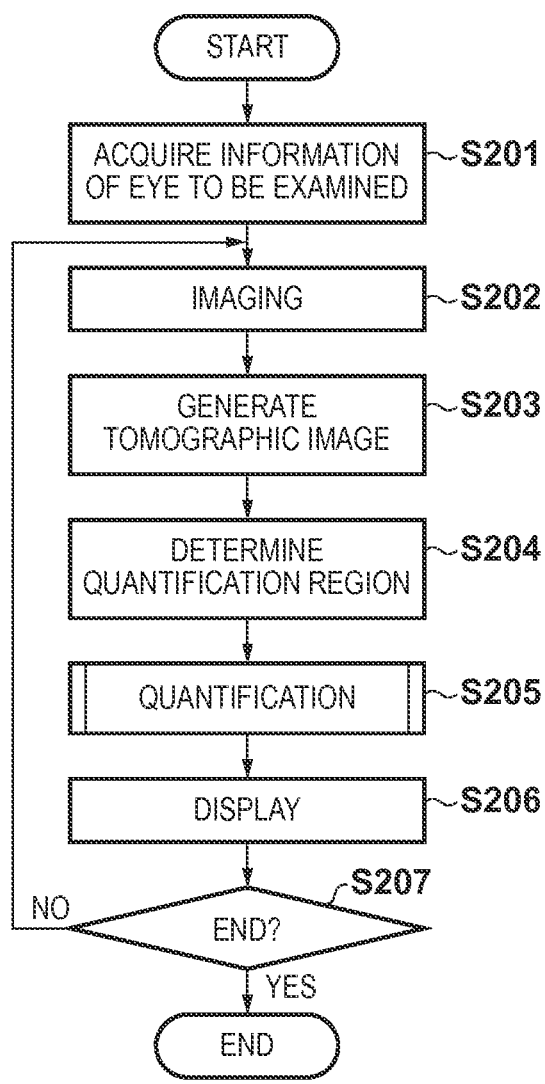
FIGS. 2A and 2B are flowcharts showing processing of the image processing system according to the first embodiment.
Figure 2B:
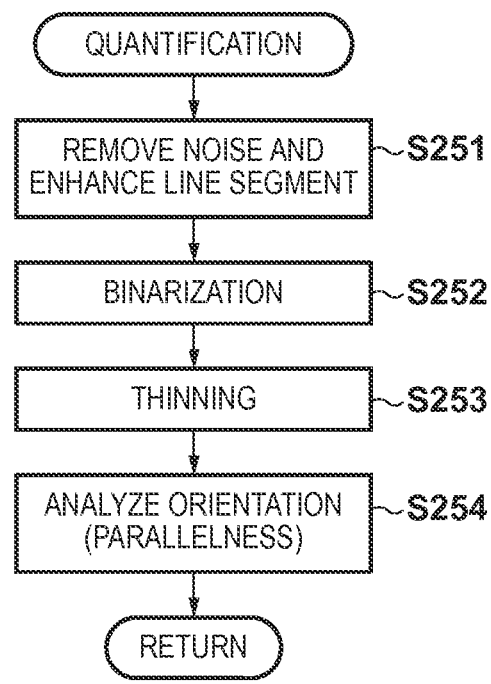

The external storage unit 500 holds pieces of information (the name, age, gender, and the like of the patient) about an eye to be examined, captured image data, imaging parameters, image analysis parameters, and parameters set by the operator in association with each other. The input unit 700 is, for example, a mouse, a keyboard, or a touch operation screen. The operator inputs instructions to the image processing apparatus 300, the tomography imaging apparatus 200, and the fundus imaging apparatus 400 via the input unit 700. The processing procedure of the image processing apparatus 300 according to this embodiment will be described next with reference to FIGS. 2A and 2B. FIG. 2A is a flowchart showing the procedure of operation processing of the entire system according to this embodiment.

<Step S201>

In step S201, an eye information acquisition unit (not shown) of the image processing apparatus 300 externally acquires a subject identification number as information used to identify an eye to be examined. The eye information acquisition unit may be configured using the input unit 700. Based on the subject identification number, the eye information acquisition unit acquires information about the eye held by the external storage unit 500 and stores it in the storage unit 302.

<Step S202>

In step S202, fundus imaging by the fundus imaging apparatus 400 and tomographic image acquisition by the tomography imaging apparatus 200 are performed based on instructions from the instruction unit 304.

The instruction unit 304 sets the imaging parameters, and the tomography imaging apparatus 200 performs imaging. More specifically, the on positions in the display unit 241 of the internal fixation lamp 204, the measurement light scan pattern by the galvanometer mirror 201, and the like are set. In this embodiment, the driving control unit 202 controls the light-emitting diodes of the display unit 241 and sets the position of the internal fixation lamp 204 so as to perform imaging at the center of a macular portion. This aims at capturing a portion near the fovea related to the eyesight. As the scan pattern, for example, cross scan or radial scan is used. In each scan pattern, the same portion is continuously captured a plurality of times to generate a high-quality tomographic image in which speckle noise is reduced or removed. After the imaging parameters are set, the tomographic image of the eye is captured. The tomography imaging apparatus 200 controls the driving control unit 202 to operate the galvanometer mirror 201 and capture the tomographic image. As described above, the galvanometer mirror 201 includes an X scanner in the horizontal direction and a Y scanner in the vertical direction. For this reason, changing the direction of each scanner enables scanning of a corresponding one of the horizontal direction (X) and the vertical direction (Y) on the coordinate system of the apparatus. When the directions of the scanners are changed at the same time, scan can be performed in the composite direction of the horizontal direction and the vertical direction. This allows scanning in an arbitrary direction on the fundus plane.

<Step S203>

In step S203, the tomographic image generation unit 311 acquires the signal data of the tomographic image captured by the tomography imaging apparatus 200 and performs signal processing to generate a tomographic image. A case in which, for example, an SS-OCT is used as the tomography imaging apparatus 200 will be explained. First, the tomographic image generation unit 311 removes fixed noise from the signal data. Next, the tomographic image generation unit 311 performs spectral shaping and dispersion compensation and applies discrete Fourier transformation to the signal data, thereby obtaining intensity data for the depth. The tomographic image generation unit 311 performs processing of cutting out an arbitrary region from the intensity data after the Fourier transformation, thereby generating a tomographic image.

At the time of tomographic image generation, to obtain a high-quality tomographic image in which speckle noise is reduced or removed, a plurality of tomographic images preferably are obtained by capturing the same portion and composed to generate one tomographic image. Hence, to generate one high-quality tomographic image, the composition unit 312 first aligns the plurality of tomographic images. To align the tomographic images, for example, an evaluation function representing the similarity of two tomographic images is defined in advance, and the tomographic images are deformed to obtain the best value of the evaluation function. Evaluation is done using, for example, a correlation coefficient as the evaluation function. Image deformation processing is performed by, for example, translation or rotation using affine transformation.

Next, the composition unit 312 performs composition processing to generate one tomographic image from the plurality of aligned tomographic images. An example of the method is averaging. In averaging, the intensity values of a plurality of pixels at the same coordinates are averaged in the plurality of aligned tomographic images. The average value is defined as the intensity value at the coordinates. When the same processing is executed at all coordinates, one high-quality tomographic image can be obtained from the plurality of tomographic images. Note that, for example, median processing may be performed in place of the averaging. In this case, the median of the intensity values of the plurality of pixels at the same coordinates is calculated in the plurality of aligned tomographic images. The median is defined as the intensity value at the coordinates. When the same processing is executed at all coordinates, one high-quality tomographic image can be obtained from the plurality of tomographic images, like the averaging. The tomographic image obtained here is stored in the storage unit 302 and also displayed on the display unit 600 in step S206 to be described later.

<Step S204>

Figure 3:
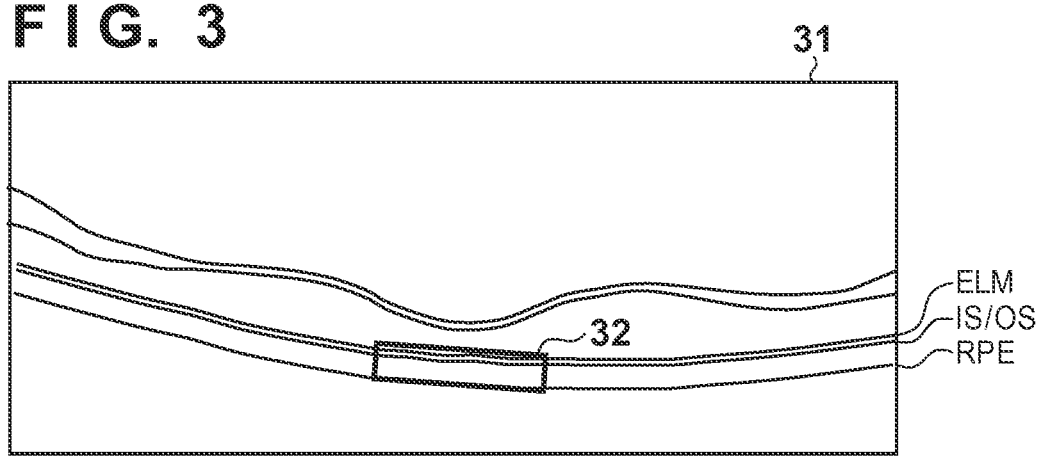
FIG. 3 is a view for explaining a quantification region.

In step S204, the quantification region determination unit 331 sets a processing target region (to be referred to as a quantification region hereinafter) in a photoreceptor layer near the fovea on the tomographic image acquired by the image acquisition unit 301. The quantification region set in the photoreceptor layer will be described with reference to FIG. 3. FIG. 3 illustrates a tomographic image 31 of a macular portion and a quantification region 32 determined by the quantification region determination unit 331. The tomographic image 31 shows an external limiting membrane (ELM), a photoreceptor inner/outer segment (IS/OS), and a retinal pigment epithelium (RPE). In a diabetic macular edema, even if the fovea thickness has increased, the eyesight is often good as long as the IS/OS is preserved. Reversely, if the IS/OS has disappeared, the eyesight is bad. Hence, the quantification region determination unit 331 determines the depth-direction position of the quantification region so as to include the IS/OS of the visual cell. The quantification region determination unit 331 also sets the location of the quantification region 32 so as to include the fovea. The size of the quantification region 32 is, for example, 150 μm in the vertical direction×1 mm in the horizontal direction. The tilt of the quantification region 32 is determined by rotating it in accordance with the tilt of the retinal layer. Note that the quantification region 32 is set on the fovea because the fovea is an important portion that reflects the eyesight best and is not affected by laser treatment and the like.

An example of a detailed method of determining the quantification region 32 will be described. First, the central position is determined based on the fixation lamp position at the time of imaging. When the imaging is performed by aligning the fixation lamp with the fovea of the macular portion, the fovea is located at the center of the tomographic image in the widthwise direction. The quantification region 32 is set so as to include the fovea based on the widthwise center of the tomographic image. The depth-direction position of the quantification region 32 is determined by detecting the RPE from the tomographic image. As the method, for example, a median filter and a Sobel filter are applied to the tomographic image 31 to create images (to be referred to as a median image and a Sobel image hereinafter). A profile is created for every A-scan from the created median image and Sobel image. A luminance value profile is obtained from the median image, and a gradient profile is obtained from the Sobel image. The peak in the profile created from the Sobel image is detected. The profile of the median image corresponding to portions before and after the detected peak or a portion between the peaks is referred to, thereby detecting the boundaries between regions of the retinal layer. A layer boundary located at a deep portion of the tomographic image is defined as the RPE. The tilt (rotation) of the quantification region 32 is determined based on the detected RPE. As the method, the slope of a linear function approximating the RPE is obtained from the coordinate values of the previously detected RPE within the range near the fovea, for example, within the range of 1 mm from the widthwise center of the tomographic image, thereby determining the tilt of the retinal layer.

The method of causing the quantification region determination unit 331 to automatically determine the quantification region 32 has been described here. However, the present invention is not limited to this. For example, the operator may perform a user operation using the input unit 700 and correct or designate the position or tilt of the quantification region 32. In this case, preferably, the operator is allowed to only designate the position of the quantification region 32 and rotate it. The size of the quantification region 32 is preferably automatically determined based on the vertical and horizontal resolutions of tomographic images obtained using the tomography imaging apparatus 200 and the image acquisition unit 301 and is displayed. For example, when one pixel has a size of 10 μm in the horizontal direction×5 μm in the vertical direction, the size of the quantification region is 100 pixels in the horizontal direction×30 pixels in the vertical direction. When the operator has changed the position of the quantification region 32 using the input unit 700, quantification processing is performed at the position after the change. Note that if the quantification region 32 is stored in a storage unit, or the region to be quantified itself is acquired as a tomographic image, all regions are analyzed. Hence, this process need not be performed.

In the embodiment, a region including a retinal pigment epithelium (RPE) is extracted from the tomographic image, and the extracted region is utilized as the quantification region 32 that includes the photoreceptor layer. However, it is not necessary to determine whether the quantification region 32 includes the photoreceptor layer. The quantification region 32 may be determined to include the detected retinal pigment epithelium (RPE).

<Step S205>

In step S205, the quantification unit 332 performs processing in the quantification region 32 determined by the quantification region determination unit 331. This method will be described with reference to FIGS. 2B and 4A to 4C.

<Step S251>

Figure 4A:
FIGS. 4A to 4C are views for explaining an example of quantification processing.

In step S251, the quantification unit 332 performs noise removal and line segment enhancement using a DoG (Difference of Gaussian) filter. The DoG filter is represented by $$D(x, y, \sigma) = (G(x, y, k\sigma) - G(x, y, \sigma)) * I(x, y) \quad (1)$$

$$G(x, y, \sigma) = \frac{1}{2\pi\sigma^2} \exp\left(-\frac{(x^2 + y^2)}{2\sigma^2}\right)$$

where D is the DoG image, G is the Gaussian function, I is the input image, σ is the scale, and k is the increasing rate. Since the image obtained by the DoG filter changes depending on σ upon calculation, the calculation is done based on the resolution per pixel of the tomographic image and a size suitable for the thickness of the layer to be detected. FIG. 4A shows the image of the processing result.

<Step S252>

Figure 4B:
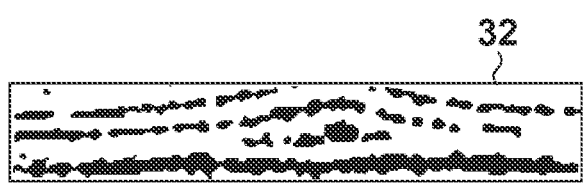

In step S252, the quantification unit 332 performs binarization using discriminant analysis in the quantification region 32 that has undergone the noise removal and line segment enhancement in step S251. FIG. 4B shows the image of the processing result. Discriminant analysis is a method of creating the intensity value histogram of the tomographic image in the quantification region 32 and determining a threshold t capable of best separating two classes obtained by dividing the distribution.

<Step S253>

Figure 4C:
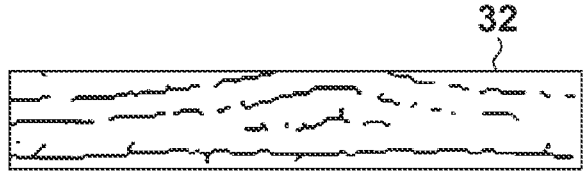

In step S253, the quantification unit 332 performs thinning from the binary image in the quantification region 32 binarized in step S252 and converts the layer into a linear structure. FIG. 4C shows the image of the processing result. In this embodiment, thinning is performed by 8-connection. This aims at holding the information of the line segment structure in oblique directions as well.

<Step S254>

In step S254, the quantification unit 332 analyzes the parallelness of the linear structure in the quantification region 32 thinned in step S253, thereby quantifying the layer structure. The parallelness of the linear structure can be calculated using, for example, $$P = \frac{|n_0 - n_{90}| + |n_{45} - n_{135}|}{n_0 + n_{45} + n_{90} + n_{135}} \quad (2)$$

In equation (2), each of $n_0$, $n_{45}$, $n_{90}$, and $n_{135}$ represents the frequency the thinned linear structure is concatenated to the adjacent pixel at the corresponding angle. For example, if a set of pixels adjacent in the horizontal direction exists, $n_0$ is 1. If a set of pixels adjacent in the vertical direction exists, $n_{90}$ is 1. That is, pixel concatenations are counted for all pixels of the linear structure in the quantification region 32, thereby obtaining $n_0$, $n_{45}$, $n_{90}$, and $n_{135}$. If the linear structure is completely random, equation (2) is 0. If the linear structure is completely parallel, equation (2) is 1. Hence, equation (2) represents the degree of distortion in the linear structure.

<Step S206>

Figure 5:
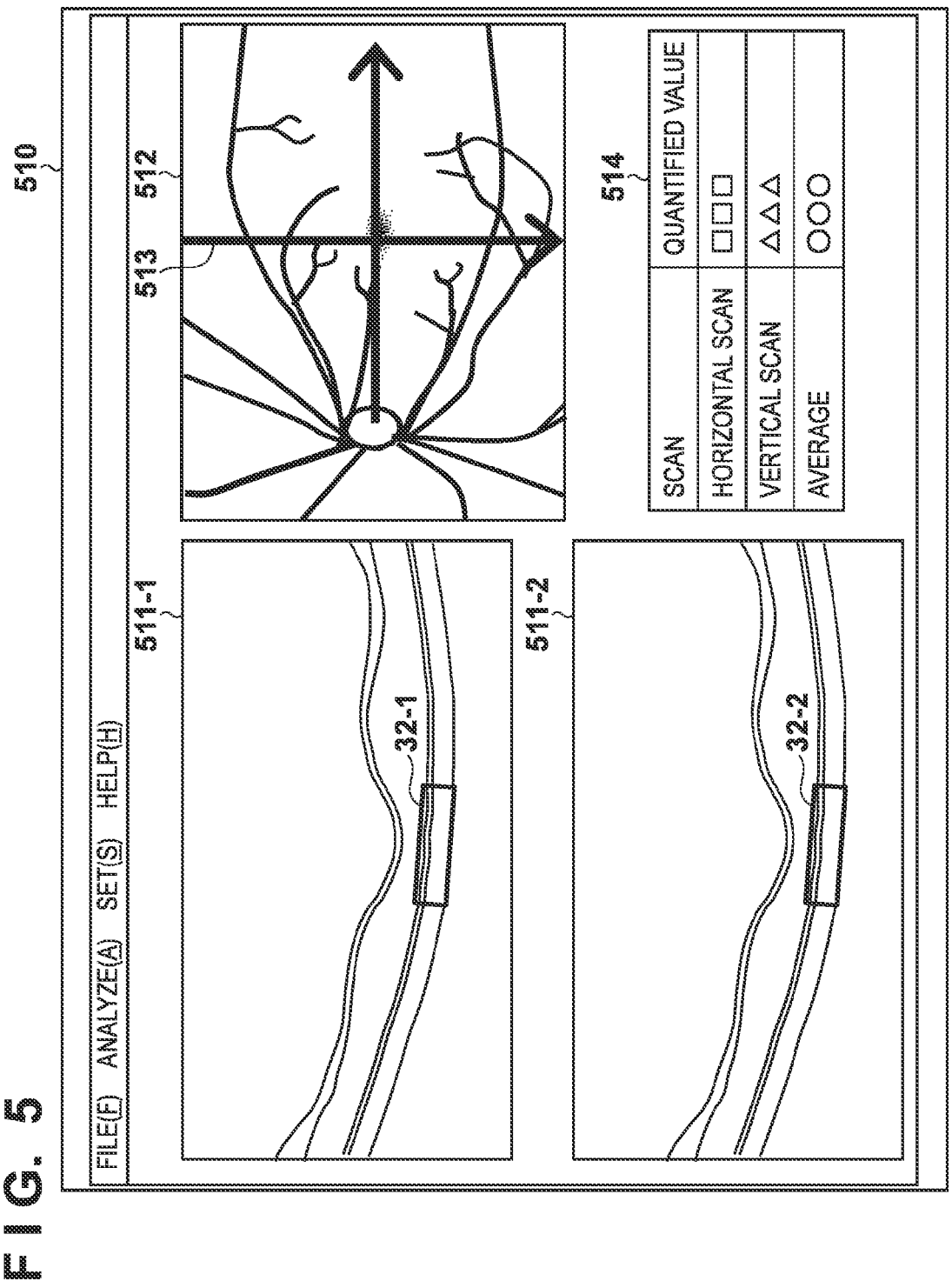
FIG. 5 is a view showing an example of analysis result display.

Referring back to FIG. 2A, in step S206, the display control unit 305 displays, on the display unit 600, the tomographic image acquired by the image acquisition unit 301 and the quantified numerical values obtained in step S245. FIG. 5 shows an example of the display. FIG. 5 illustrates an example in which imaging is performed by cross scan, and the scan data is quantified. Referring to FIG. 5, reference numeral 510 denotes a tomographic image observation screen; 511-1, a tomographic image obtained by scanning in the horizontal direction; 511-2, a tomographic image obtained by scanning in the vertical direction; 32-1 and 32-2, examples of the quantification region identifiably superimposed on the tomographic images; 512, a fundus image captured by the fundus imaging apparatus 400; 513, a scan pattern of the tomography imaging apparatus 200 superimposed on the fundus image 512; and 514, an example of display of quantified numerical values. In the cross scan, quantified values in the respective scans and the average value thereof are displayed. When the number of scans is large, as in radial scan, only the average value may be displayed. Note that the superimposed display of the scan pattern on the fundus image 512 captured by the fundus imaging apparatus 400 is done based on, for example, the information of the imaging position on the fundus by the fundus imaging apparatus 400 and the information of the imaging position on the fundus by the tomography imaging apparatus 200.

<Step S207>

In step S207, an instruction acquisition unit (not shown) externally acquires an instruction representing whether to end the tomography imaging by the image processing system 100. This instruction is input by the operator using the input unit 700. Upon acquiring an instruction to end the processing, the image processing system 100 ends the processing. On the other hand, to continue the imaging, the process returns to step S202 to continue the imaging. When shifting the process to another step, if the operator has corrected the position or tilt of the quantification region 32 in step S204 but not saved the result in the external storage unit 500, a confirmation dialogue is displayed to confirm whether to save the change result in the external storage unit 500. If the operator selects to save, the parameters changed by the operator are saved in the external storage unit 500. If the operator selects not to save, the parameters changed by the operator are not saved in the external storage unit 500.

The processing of the image processing system 100 is performed in the above-described way.

According to the above-described arrangement, it is possible to quantify a complex structural change in the photoreceptor layer, which affects the visual performance. This allows judgment of the degree of progression of a disease or execution of treatment, or quantitative judgment of the degree of recovery after treatment.

Second Embodiment

Fractal Analysis

In the first embodiment, an example has been described in which the quantification unit 332 thins the layer in the quantification region 32 and calculates the parallelness of the lines, thereby quantifying the degree of distortion in the layer. In the second embodiment, as an example in which the degree of distortion in a layer is quantified by another method, a method using fractal analysis will be explained. Note that in this embodiment, processing concerning quantification (step S205 of FIG. 2A) by a quantification unit 332 shown in FIG. 1 is different from the first embodiment. The remaining processes are the same as in the first embodiment, and a description thereof will be omitted.

To perform fractal analysis, the quantification unit 332 performs noise removal, line segment enhancement, and binarization as in steps S251 and S252. The quantification unit 332 then executes fractal analysis in a binarized quantification region 32. As the fractal analysis, fractal dimensions (by Box-counting) and lacunarity are obtained as complexity. The fractal dimensions are obtained by covering the quantification region 32 with boxes of an arbitrary size ($\epsilon$) and counting the number N of boxes including the quantification region. $\epsilon$ is changed in a wide range, and N for each $\epsilon$, that is, N($\epsilon$) is obtained. This is shown by:

$$N = A\varepsilon^{-D_F} \quad (3)$$
$$D_F = \frac{\log N}{\log \varepsilon}$$

where A is a constant, and $D_F$ is the fractal dimension. In a complex pattern, when the box becomes small, many uneven portions are included, and the fractal dimension becomes large. On the other hand, the lacunarity is an index representing how much the fractals fill the space and is used to classify a fractal having the same fractal dimension but a different degree of gaps in the space. The lacunarity can be obtained by arranging a plurality of boxes of the size $\epsilon$ in the quantification region 32 and calculating the average of coefficients CV of variation in the number of pixels included in the boxes. The lower the lacunarity is, the higher the density is. The higher the lacunarity is, the larger the gap is. Hence, when the layers in the quantification region 32 are periodically arranged, the value of the fractal dimension is large, and the numerical value of the lacunarity is small. If the layer structure in the quantification region 32 is distorted or lost, the value of the fractal dimension is small, and the numerical value of the lacunarity is large.

Third Embodiment

Analysis of Statistical Features of Texture

In the second embodiment, a method using fractal analysis as texture features has been described. In the third embodiment, a method using statistical features of texture will be explained. Note that in this embodiment, processing concerning quantification (step S205 of FIG. 2A) by a quantification unit 332 shown in FIG. 1 is different from the first embodiment. The remaining processes are the same as in the first embodiment, and a description thereof will be omitted.

The statistical features of texture characterize the texture by the statistical properties concerning the density distribution of a pixel set. In a healthy eye, the layers from the IS/OS to the RPE near the fovea of the macular portion are periodically arranged. On the other hand, if the eyesight is poor because of a diabetic macular edema, the layer structure from the IS/OS to the RPE is often lost or distorted. Hence, analyzing whether the layers in this region are periodically arranged allows performance of quantification.

To calculate a texture feature amount, the quantification unit 332 flattens the histogram in a quantification region 32 and normalizes the average value or variance of intensity values and simultaneously, to reduce the processing load, converts the number of levels of the intensity values of the image into n=about 16. Additionally, to correct the tilt of the image in the quantification region 32, the image is rotated so make the retinal layer parallel in the horizontal direction.

(1) Texture Feature Amount Calculation Using Run-Length Matrix

The quantification unit 332 calculates, for example, a run-length matrix as a texture feature amount. A run-length matrix having, as an element, a frequency $P_\theta(i, m)$ m points having an intensity value i continue in a $\theta$ direction (i=0, 1, 2, . . . , n−1, m=1, 2, . . . , 1) in the image is obtained, and feature amounts represented by $$f_1 = \sum_{i=0}^{n-1} \sum_{m=1}^{1} \frac{P_\theta(i, m)}{m^2} \bigg/ \sum_{i=0}^{n-1} \sum_{m=1}^{1} P_\theta(i, m) \quad (4)$$

$$f_2 = \sum_{i=0}^{n-1} \sum_{m=1}^{1} m^2 P_\theta(i, m) \bigg/ \sum_{i=0}^{n-1} \sum_{m=1}^{1} P_\theta(i, m) \quad (5)$$

are calculated from the matrix. Equation (4) takes a large value as the short run occurrence frequency is high, and equation (5) takes a large value as the long run occurrence frequency is high. That is, if the layers in the quantification region 32 are periodically arranged, the value of equation (4) is small, and the value of equation (5) is large. If the layer structure in the quantification region 32 is distorted or lost, the value of equation (4) is large, and the value of equation (5) is small. FIG. 6 shows an example of the screen displayed on a display unit 600 in this case. Referring to FIG. 6, 614 represents an example in which quantified numerical values are displayed. In the example 614, the value of equation (5) is displayed as the degree of continuity of a layer, and the value of equation (4) is displayed as the degree of loss of continuity of a layer. Note that when the degree of continuity of a layer or the degree of loss of continuity of a layer is obtained assuming that θ is the horizontal direction that is the direction of the retinal layer, the intermittence of the layer can be known. However, when the degree of continuity or the degree of loss of continuity of a layer is obtained for another θ (45° or 90°), the variation (distribution) of the depth-direction position of the photoreceptor layer (in an intermittent layer) can be obtained.

(2) Texture Feature Amount Calculation Using Cooccurrence Matrix

As the texture feature amount, for example, a cooccurrence matrix feature may be calculated. A cooccurrence matrix having, as an element, a probability that the intensity value of a point spaced apart from a point having the intensity value i by a predetermined displacement δ=(r, θ), that is, by r in the direction of the angle θ in the image is obtained. Note that since each element of the matrix includes a frequency, normalization is performed such that the sum of the elements becomes 1. From the cooccurrence matrix, a feature amount represented by $$q_1 = \sum_{i=0}^{n-1} \sum_{j=0}^{n-1} \{P_\delta(i, j)\}^2 \quad (6)$$

is obtained. Equation (6) represents the angular second moment. In equation (6), for example, feature amount calculation of displacement δ=(1, 0°) is performed. The feature amount of equation (6) represents the total evenness. The cooccurrence matrix also allows calculation of a plurality of feature amounts such as contrast, variance, and correlation other than equation (6) and need not always be limited to the above-described feature amount.

(3) Texture Feature Amount Calculation Using Fourier Transformation

The texture feature amount may be obtained by Fourier-transforming the image and obtaining a texture feature from the distribution of the frequency components, in place of the feature amount in the image space. A power spectrum p(u, v) and its polar coordinates P(θ, r) are obtained using a result F(u, v) of two-dimensional Fourier transformation, and features given by $$(\theta) = \sum_{\theta'=\theta-\frac{\Delta\theta}{2}}^{\theta+\frac{\Delta\theta}{2}} \sum_{r=0}^{\infty} P(\theta', r) \quad (7)$$

$$P(r) = \sum_{r'=r-\frac{\Delta r}{2}}^{r+\frac{\Delta r}{2}} \sum_{\theta=0}^{2\pi} P(\theta, r') \quad (8)$$

are calculated. Equation (7) extracts a frequency component in the direction of the angle θ, which has a width Δθ in the image. Equation (8) extracts a component of a frequency r having a width Δr. The large numerical value of equation (7) means that there is a texture pattern whose intensity value largely changes in the θ direction. Hence, a wave group in the vertical direction is formed in the retinal layer having a layer structure in the horizontal direction. If the retinal layer structure is distorted due to a disease, an irregular wave group is detected.

(4) Texture Feature Amount Calculation Using Steerable Filter

As another quantification method using a texture feature amount, a method using an image direction or a spatial frequency structure such as a Steerable filter may be used. The Steerable filter is a filter having a directivity in an arbitrary direction. Examples of the Steerable filter are a Steerable filter $G_2^\theta$ of a second order derivative $G_2$ of a Gaussian function given by $$G_2^\theta = k_a(\theta)G_{2a} + k_b(\theta)G_{2b} + k_c(\theta)G_{2c} \quad (9)$$

and a Steerable filter $H_2^\theta$ of $H_2$ having the same filter frequency response as that of $G_2$ and a phase different by 90°, which is given by $$H_2^\theta = l_a(\theta)H_{2a} + l_b(\theta)H_{2b} + l_c(\theta)H_{2c} \quad (10)$$

In equations (9) and (10), the Steerable filters are expressed by linear combinations of three basis filter ($G_{2a}$, $G_{2b}$, $G_{2c}$, $H_{2a}$, $H_{2b}$, $H_{2c}$) and their interpolation coefficients ($k_a$, $k_b$, $k_c$, $l_a$, $l_b$, $l_c$). Using these equations, the image direction can be detected by a direction energy $E^\theta$ given by $$E_n^\theta = [g_n^\theta]^2 + [h_n^\theta]^2 \quad (11)$$

where $g_n^\theta$ represents the convolution operation of $G_n^\theta$ and an image I. Similarly, $h_n^\theta$ represents the convolution operation of $H_n^\theta$ and the image I. The subscript n represents the nth order derivative of the Gaussian function. Direction detection can be done in the direction θ in which equation (11) takes the maximum value. By equation (11), the direction of each pixel in the quantification region 32 can be obtained. A line edge and a step edge can be obtained from the image using the direction components. The degree of distortion in a photoreceptor layer can be quantified by obtaining the variance of the direction energy on the line edge or the variance of the direction energy on the step edge. That is, in a retinal layer having a layer structure in the horizontal direction, the variance is small. If the retinal layer structure is distorted due to a disease, the variation is large.

According to the above-described arrangement, it is possible to quantify the degree of distortion in the photoreceptor layer near the fovea using image features.

Fourth Embodiment

Generation of Tomographic Image to be Used for Analysis

In the first embodiment, processing of causing the tomographic image generation unit 311 to acquire the signal data of a tomographic image captured by the tomography imaging apparatus 200 and perform signal processing to generate a tomographic image has been described. In the fourth embodiment, a tomographic image generation method more suitable for quantifying the degree of distortion in a photoreceptor layer will be explained. FIG. 7A shows the processing procedure of this embodiment. In this embodiment, the scan parameters at the time of imaging by the tomography imaging apparatus shown in FIG. 1 (step S702 of FIG. 7A) and processing concerning tomographic image generation by a tomographic image generation unit 311 (step S703 of FIG. 7A) are different from the first embodiment. The remaining processes are the same as in the first or second embodiment, and a description thereof will be omitted.

<Step S702>

In step S702, an instruction unit 304 sets the imaging parameters, and imaging is performed. More specifically, the instruction unit 304 determines the illumination position of an internal fixation lamp 204, the scan pattern of a galvanometer mirror 201, and the number of A scans to form one tomographic image. As for the number of A scans, imaging is performed by oversampling to reduce or remove speckle noise. Note that in this embodiment, oversampling is sampling at an interval narrower than the sampling interval for obtaining a necessary resolution. For example, when the number of A scans to finally form one tomographic image is 1,024, imaging is performed by 2,048 A scans, and adjacent A scans are synthesized.

As the scan pattern, for example, cross scan or radial scan is used. In each scan pattern, parameters may be determined to continuously capture the same portion a plurality of times to generate a high-quality tomographic image with little noise. The instruction unit 304 determines the imaging parameters and instructs to capture a tomographic image of an eye to be examined.

<Step S703>

In step S703, the tomographic image generation unit 311 acquires the signal data of a tomographic image captured by a tomography imaging apparatus 200 and performs signal processing, thereby generating a tomographic image. FIG. 7B shows this processing procedure.

<Step S731>

Figure 8A:
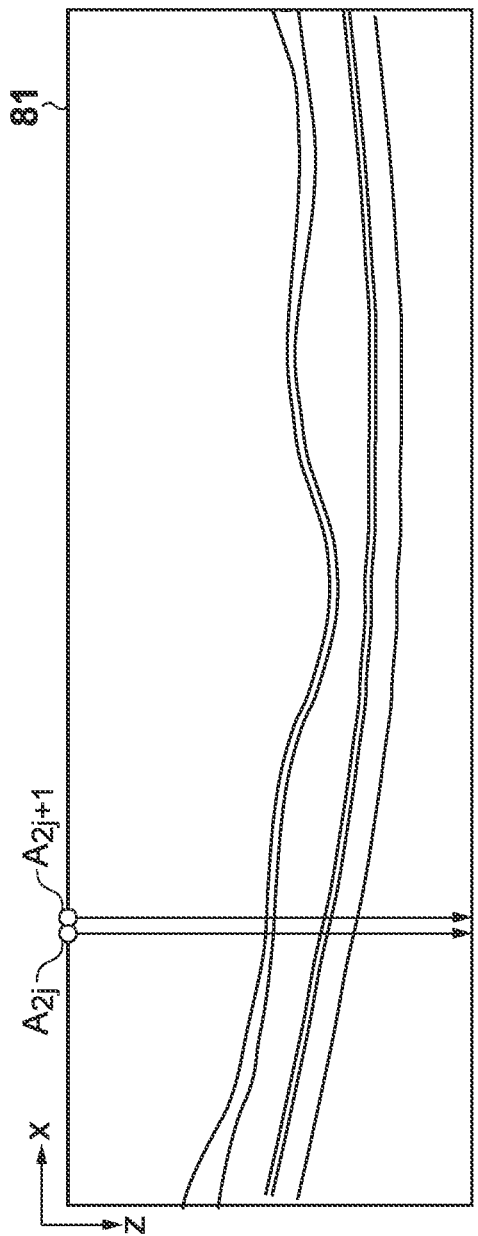
FIGS. 8A and 8B are views for explaining image generation processing according to the fourth embodiment.
Figure 8B:
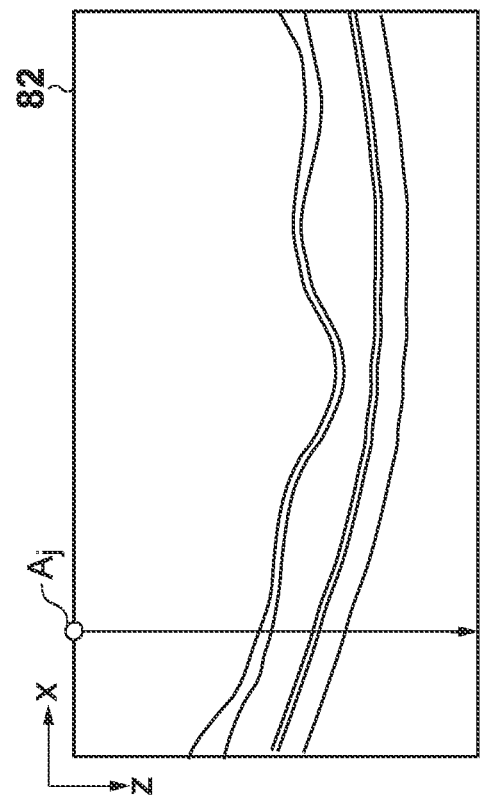

In step S731, the tomographic image generation unit 311 performs A scan synthesis in the signal data captured by oversampling at the time of imaging. FIG. 8A is a view showing a tomographic image 81 captured by oversampling. By arithmetic processing of the tomographic image 81, a new tomographic image is created. FIG. 8B is a view showing a new tomographic image 82 generated by A scan synthesis processing of the tomographic image 81 of oversampling. Referring to FIG. 8A, $A_{2j}$ and $A_{2j+1}$ represent A scans. $A_{2j+1}$ is the scan line captured 1/f [s] after the capture of $A_{2j}$. In this embodiment, when the number of A scans of oversampling is 2,048, and the number of A scans of the tomographic image to be finally obtained is 1,024, the subscript j is j=0, 1, 2, ..., 1023. FIG. 8B illustrates a tomographic image created by arithmetic processing of n pixels for each pixel. Referring to FIG. 8B, $A_j$ is a new scan line obtained by arithmetic processing of scan lines. When obtaining the scan line from FIG. 8A, $A_j$ is a scan line obtained by arithmetic processing of the scan lines $A_{2j}$ and $A_{2j+1}$. As for the arithmetic processing method, an average value, a median, or the like is calculated using an arbitrary arithmetic processing method.

<Step S732>

In step S732, the tomographic image generation unit 311 removes fixed noise from the signal data.

<Step S733>

Figure 9A:
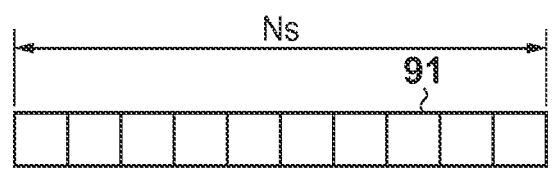
FIGS. 9A and 9B are views for explaining image generation processing according to the fourth embodiment.
Figure 9B:
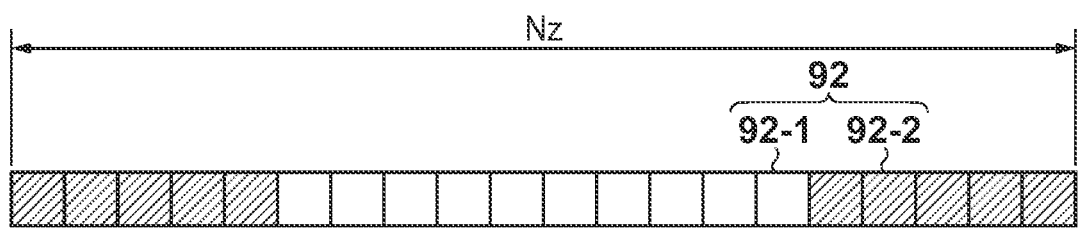

In step S733, the tomographic image generation unit 311 performs zero padding for the signal data, thereby adjusting the pixel resolution in the depth direction. This processing will be described with reference to FIGS. 9A and 9B. FIG. 9A shows signal data 91 of A scan before zero padding, and FIG. 9B shows signal data 92 of A scan after zero padding. In the signal data 92 shown in FIG. 9B, 92-1 indicates actual signal data, and 92-2 indicates an inserted zero value. In the zero padding, zero values are inserted to the two ends of the signal data, and signal data having a length designated by a parameter $N_z$ is output. The parameter $N_z$ is a power of 2. The zero padding allows improvement of the pixel resolution in the depth direction and correct grasping of the intensity and depth-direction position of a boundary where the refractive index changes. That is, improving the pixel resolution makes it possible to better separate adjacent retinal layers and more accurately calculate the parallelness. However, when zero padding is performed, subsequent processes are time-consuming. Hence, an appropriate number of zero values are preferably inserted.

<Steps S734 to S741>

Next, the tomographic image generation unit 311 performs spectral shaping (step S734) and dispersion compensation (step S735) and applies discrete Fourier transformation to the signal data (step S736), thereby obtaining intensity data for the depth. The tomographic image generation unit 311 performs processing of cutting out an arbitrary region from the intensity data after the Fourier transformation (step S737), thereby generating a tomographic image. The tomographic image generation unit 311 performs log conversion for the intensity data after the Fourier transformation (step S738) and performs normalization to fit the data to the data accuracy of the tomographic image to be output (step S739). At the time of tomographic image generation, to obtain a high-quality tomographic image in which speckle noise is reduced or removed, a plurality of tomographic images are preferably obtained by capturing the same portion and composed to generate one tomographic image. Hence, if there are a plurality of tomographic images obtained by capturing the same portion, a composition unit 312 performs composition processing of aligning the plurality of tomographic images and generating one tomographic image from the plurality of tomographic images (steps S740 and S741), as in the first embodiment. The composition processing is the same as described in the first embodiment.

Note that although this embodiment assumes that the same zero padding is performed for all signal data of the tomographic image, the present invention is not limited to this. For example, the number of zero values of zero padding may be changed between signal data near the fovea of the tomographic image and signal data of the whole tomographic image. This allows adjustment of the resolution so that the pixel resolution in the depth direction changes between the region near the fovea and the remaining regions. In this case, only signal data corresponding to the region near the fovea is copied for internal processing, and a tomographic image for the internal processing is generated. More specifically, the number (M1) of zero values per A scan to be used to generate a tomographic image for display and the number (M2) of zero values per A scan to be used to generate a tomographic image for internal processing hold a relationship M1<M2.

According to the above-described arrangement, speckle noise reduction or removal by A scan synthesis of oversampling and improvement of the pixel resolution in the depth direction by zero value are expected. For this reason, a tomographic image suitable for the processing of quantifying the degree of distortion in a photoreceptor layer near the fovea can be generated. It is therefore possible to accurately obtain the quantified numerical values.

Fifth Embodiment

Display of Analysis Result

In the first embodiment, an example has been described in which the display control unit 305 displays the tomographic image and the numerical values of quantification on the display unit 600. In the fifth embodiment, an example will be described in which a result of comparison between quantified numerical values and a statistical database stored in an external storage unit 500 and the numerical values of another test result for an eye to be examined are displayed.

Figure 10:
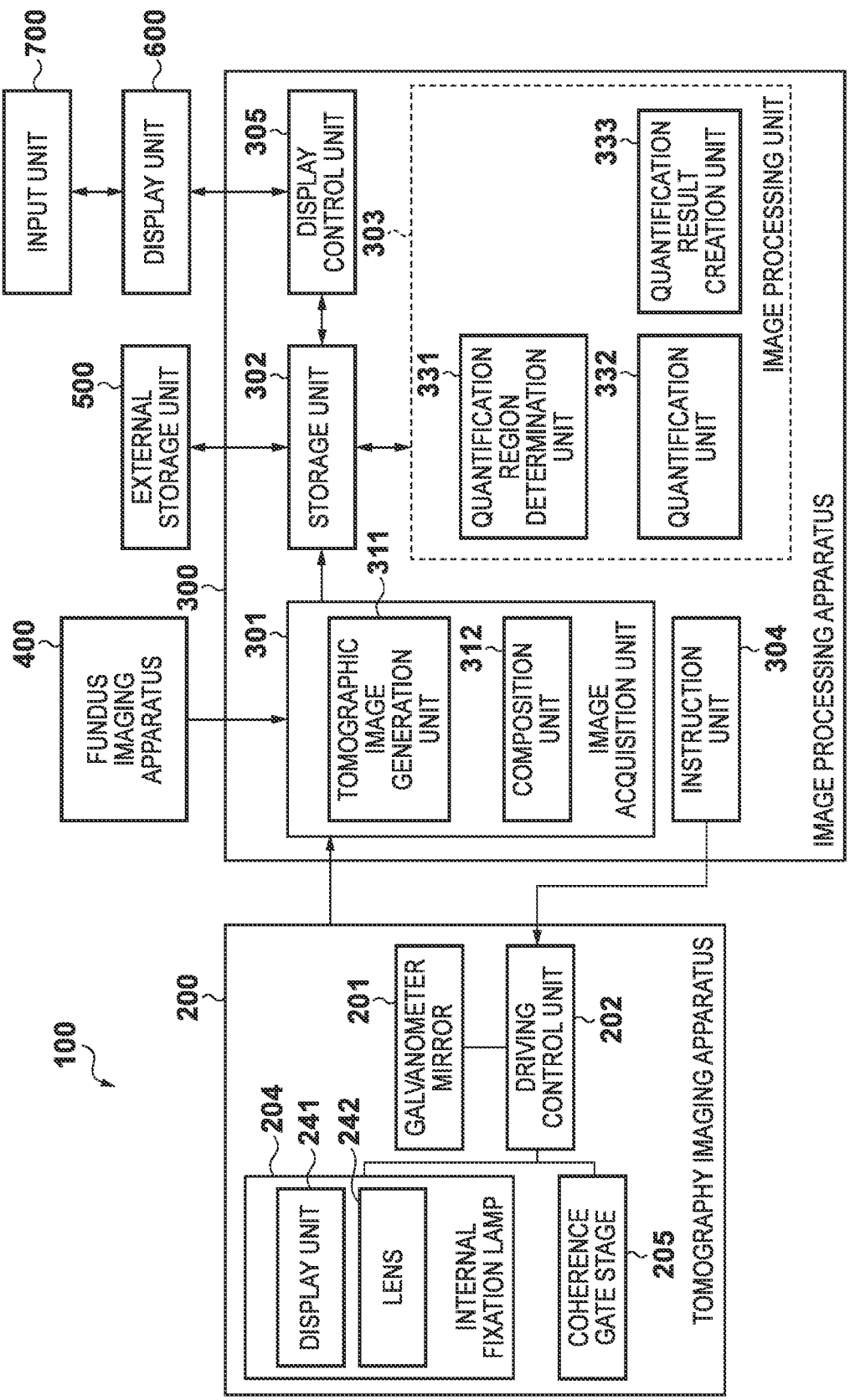
FIG. 10 is a block diagram showing the arrangement of an image processing system according to the fifth embodiment.

An example of display of an image processing system according to this embodiment will be explained with reference to FIGS. 10 and 11. Note that a description of parts having the same functions as in the first to fourth embodiments will be omitted here. FIG. 10 is a block diagram showing the arrangement of an image processing system 100 according to the fifth embodiment, which includes an image processing unit 303 including a quantification result creation unit 333, a storage unit 302, a display control unit 305, and the external storage unit 500.

In the fifth embodiment, the quantification result creation unit 333 creates a graph based on the numerical values quantified by a quantification unit 332 and statistical data stored in the external storage unit 500, and the display control unit 305 displays the result on a display unit 600 together with a tomographic image. This example will be described with reference to FIGS. 11A to 11C. FIG. 11A shows an example of a one-dimensional graph 1100-1 created by the quantification result creation unit 333 and representing a position where a quantified value exists in the statistical database. The graph 1100-1 has a scale normalized from 0.1 corresponding to the minimum value of the quantified value to 1.0 corresponding to the maximum value. In the illustrated example of the index, the numerical value becomes large for a normal state. FIG. 11A shows an example in which a region where treatment is recommended exists on the left side of a vertical line 1100-2, a region where follow-up is recommended exists between the vertical line 1100-2 and a vertical line 1100-3, and a normal region exists on the right side of the vertical line 1100-3. Reference numeral 1100-4 represents an example of a qualified numerical value of an eye plotted on the graph 1100-1. This graph visually displays a position where a quantified value exists on the statistical database and is therefore usable as a material for judging execution of treatment, follow-up, and the like.

FIG. 11B shows an example of a two-dimensional graph 1101-1 representing a position where a quantified value exists in the statistical database and a quantitative eyesight estimated from the position. FIG. 11B shows an example in which 1101-2 indicates the region on the graph 1101-1 where the quantified numerical value of the eye is included. This graph can show a result of a quantitative eyesight estimated from a distortion in a photoreceptor layer. For example, when the quantified value is a to b, the estimated eyesight is about 0.45 to 0.7 (hatched portion in FIG. 11B).

FIG. 11C shows an example of a table 1102 that displays a comparison of a result of an eyesight test acquired from the external storage unit 500 as a numerical value of another test result for the eye, a quantified value, and an eyesight estimated from the quantified value. This table allows grasping of the relationship between the quantitative eyesight estimated from a distortion in a photoreceptor layer and the eyesight obtained by the eyesight test.

Figure 12:
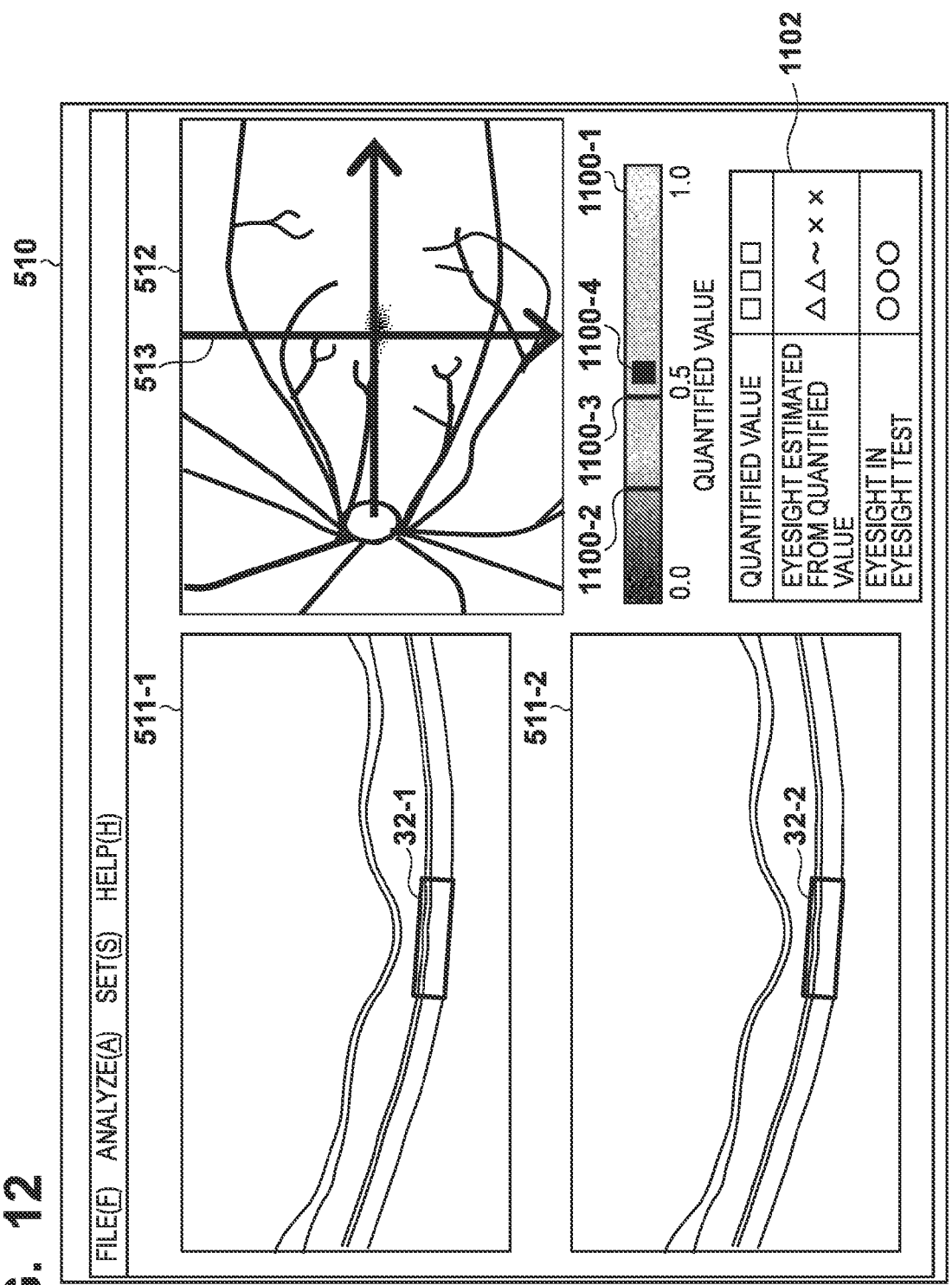
FIG. 12 is a view showing an example of analysis result display.

FIG. 12 shows an example in which the display control unit 305 displays, on the display unit 600, tomographic images and the various kinds of graphs created by the quantification result creation unit 333. FIG. 12 illustrates an example in which tomographic images 511-1 and 511-2 captured by cross scan, a fundus image 512, and the graph 1100-1 and the table 1102 created by the quantification result creation unit 333 are laid out and displayed. Note that the layout of the tomographic images, the fundus image, and the quantified values is not limited to this.

According to the above-described arrangement, the quantified value of the eye and the statistical value can be compared and examined. For this reason, the result can be used as a material for judging execution of treatment, follow-up, and the like. It is also possible to quantitatively measure the eyesight.

Sixth Embodiment

Correction of Retinal Layer Shape

In the first embodiment, a method of performing quantification for a region determined by the quantification region determination unit 331 has been described. In the sixth embodiment, an example will be described, in which the retinal layer shape is corrected (normalized) before a quantification region determination unit 331 determines a region.

Figure 13:
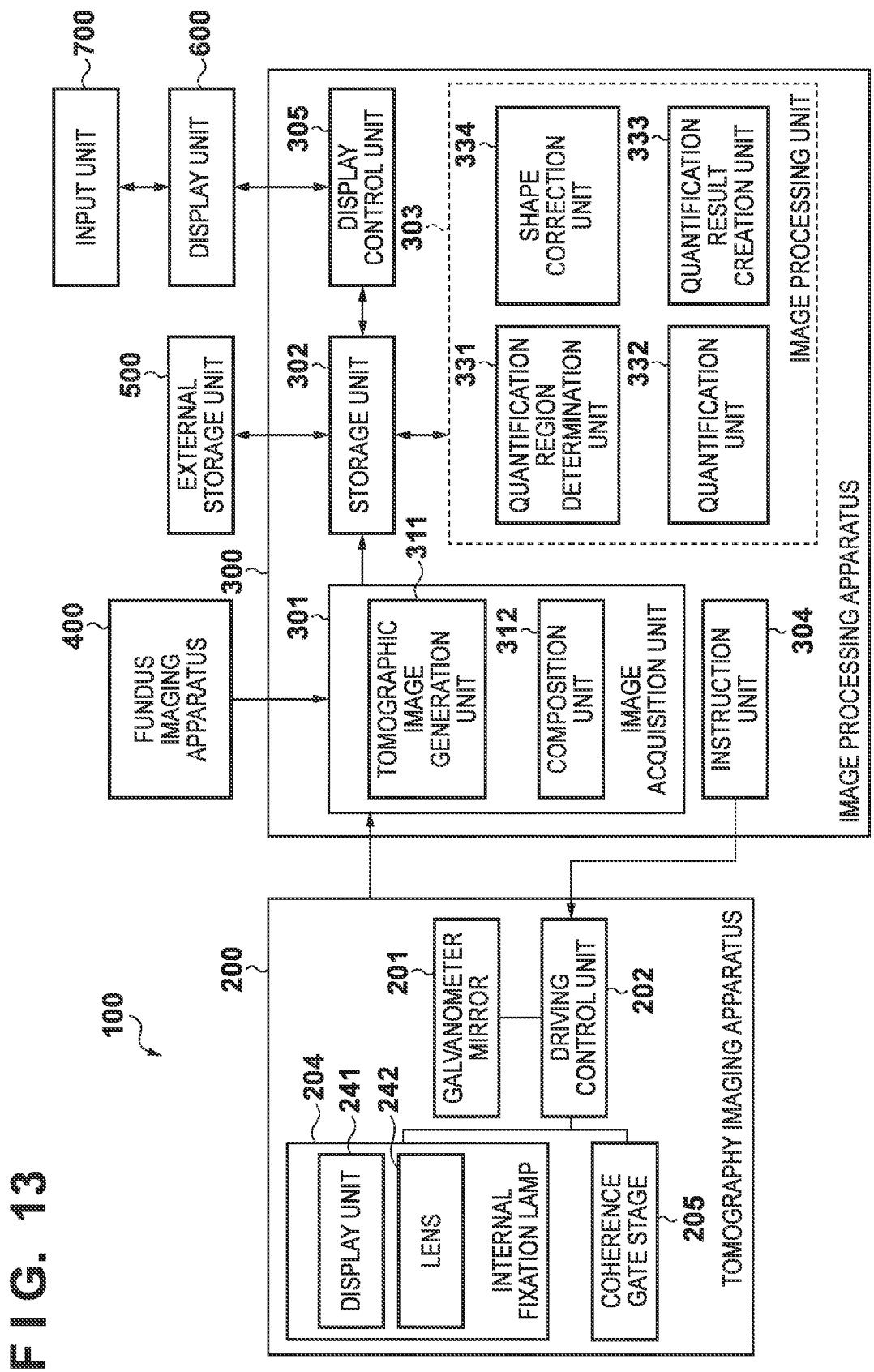
FIG. 13 is a block diagram showing the arrangement of an image processing system according to the sixth embodiment.
Figure 14:
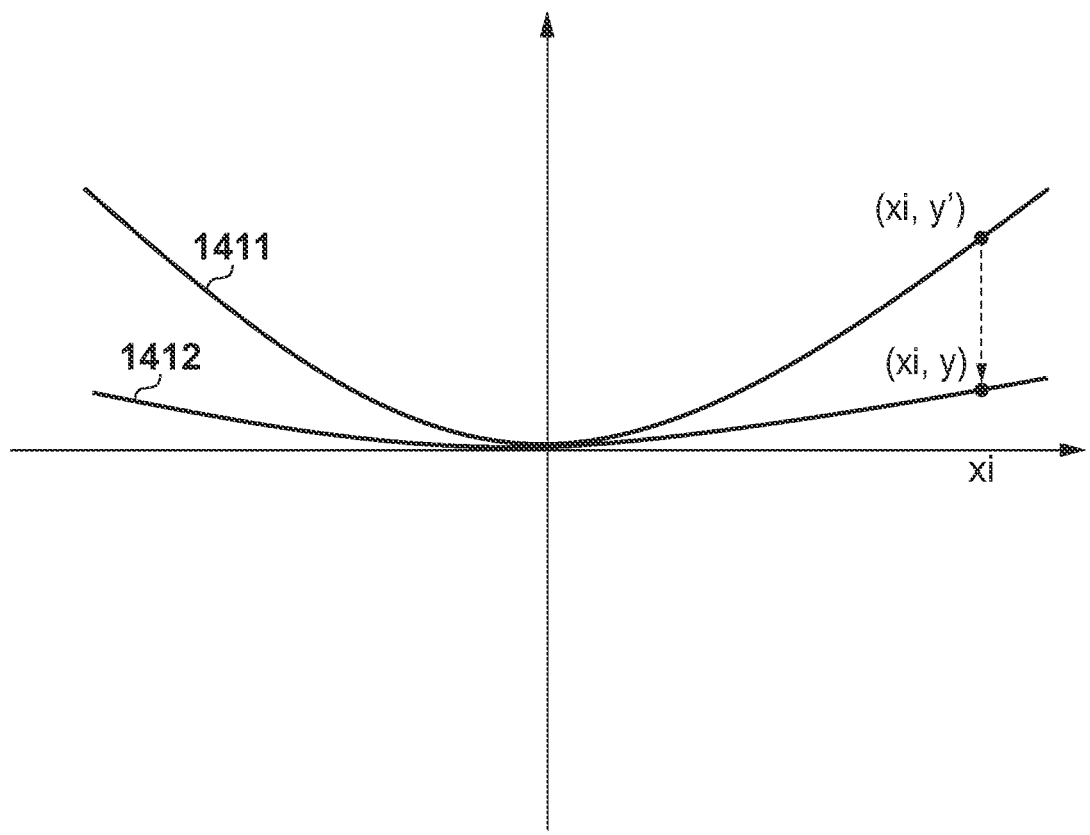
FIG. 14 is a graph for explaining shape correction.
Figure 15A:
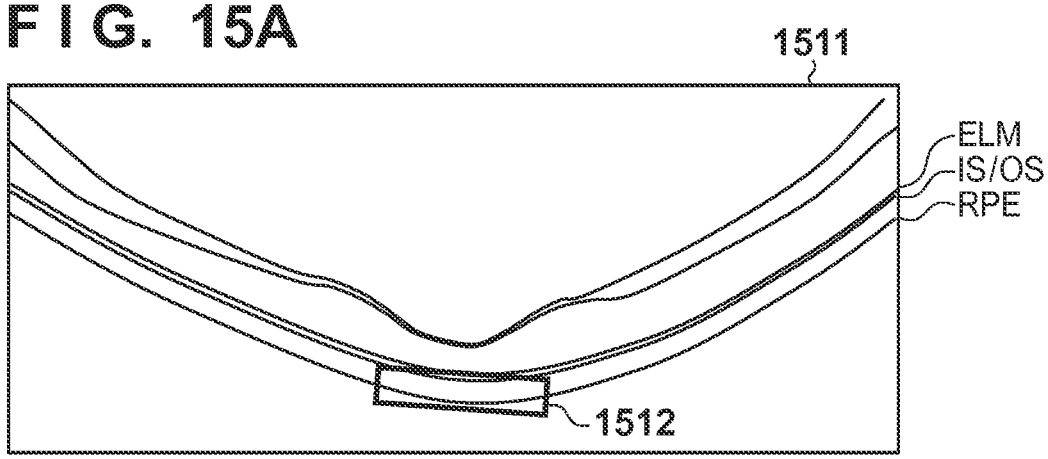
FIGS. 15A and 15B are views for explaining shape correction.
Figure 15B:
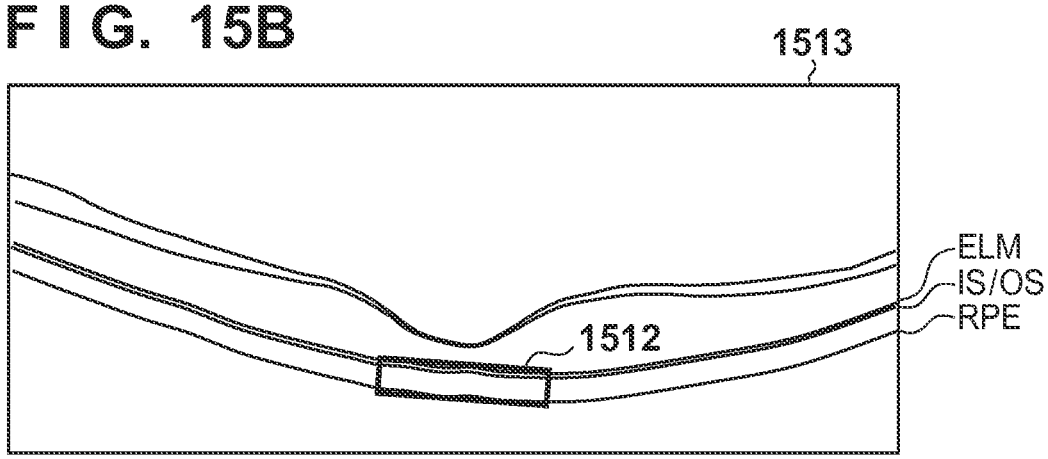

An example of the arrangement of an image processing system according to the sixth embodiment will be described below with reference to FIG. 13, and an example of display on the image processing system according to the sixth embodiment will be described with reference to FIGS. 14, 15A, and 15B. Note that a description of parts having the same functions as in the first to fifth embodiments will be omitted here. FIG. 13 is a block diagram showing the arrangement of an image processing system 100 including an image processing unit 303 including a shape correction unit 334.

In this embodiment, an example will be explained in which the shape correction unit 334 corrects the shape of a retinal layer. Performing shape correction and normalizing the retinal layer shape enables stable quantification of the degree of distortion in a photoreceptor layer even in a retinal layer shape largely curved due to nearsightedness.

As the shape correction method, the shape correction unit detects an RPE from a retinal layer. As the detection method, a retinal layer boundary can be detected by the method described concerning step S204 of the first embodiment. When a tomography imaging apparatus 200 is PS-OCT, the RPE can be detected by calculating a polarized light component. RPE detection from a tomographic image captured by PS-OCT can be done by using, for example, DOPU (Degree Of Polarization Uniformity) described in Erich Gotzinger, "Retinal pigment epithelium segmentation by polarization sensitive optical coherence tomography" (literature 2).

The RPE detected using these methods is approximated to a quadratic function. The approximation is performed by removing outliers using a robust estimation method such as M-estimation. The approximated quadratic function ($y=a'x^2+b'x+c'$) is converted into a quadratic function ($y=ax^2+bx+c$) serving as a reference. FIG. 14 shows the relationship of coordinates. A curve 1411 is an example of an approximated curve obtained from the RPE. A curve 1412 is an example of a curve serving as a reference. At $x_i$, coordinates ($x_i$, $y_i$) are converted into coordinates (x, y). When the same processing is executed at all x-coordinates, the y-coordinates can be converted. If the curve of the retinal layer is large, the layers from the IS/OS to the RPE cannot be included in the quantification region, and a measurement error occurs. However, when the shape is corrected, the quantification region can include the layers from the IS/OS to the RPE in both a retinal layer shape having a large curve and a retinal layer shape having a small curve. This enables more stable measurement. FIGS. 15A and 15B show examples of retinal layer shapes deformed by retinal layer shape correction. FIG. 15A shows an example of a tomographic image 1511 before shape correction and a quantification region 1512. FIG. 15B shows an example of a tomographic image 1513 corrected to a reference shape and the quantification region 1512.

Figure 16:
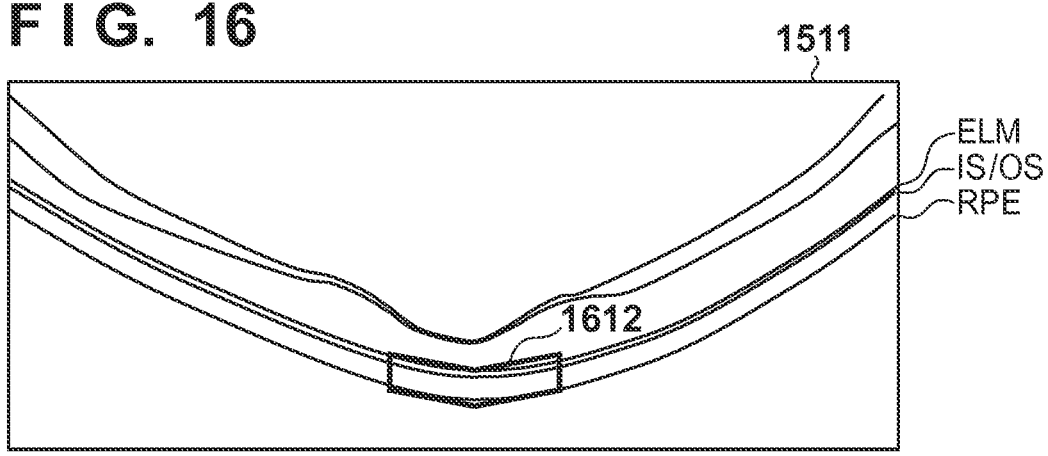
FIG. 16 is a view for explaining quantification region correction.

In this embodiment, an example in which the entire retinal layer shape is corrected has been described. However, the present invention is not limited to this. For example, not the entire retinal layer shape only the retinal layer shape in the quantification region may be corrected. FIG. 16 shows an example. FIG. 16 illustrates the tomographic image 1511 and a quantification region 1612. FIG. 16 shows an example in which the shape of the quantification region 1612 is corrected in accordance with the retinal layer shape of the tomographic image. More specifically, the quantification region is corrected so as to conform to the curve obtained by approximating the RPE to a quadratic function as described above, thereby obtaining the corrected quantification region 1612. The quantification region 1612 deformed so as to conform to the retinal layer shape is returned to a rectangular shape as indicated by the quantification region 1512, and the tomographic image in the quantification region is also corrected.

According to the above-described arrangement, the retinal layer shape is normalized. This allows stable quantification of the degree of distortion in a photoreceptor layer in both a retinal layer shape having a large curve due to nearsightedness or the like and a retinal layer shape having a moderate curve in a normal eye.

Other Embodiments

Each of the above-described embodiments implements the present invention as an image processing apparatus. However, the embodiments of the present invention are not limited to the image processing apparatus. For example, the present invention can take a form of a system, an apparatus, a method, a program, a storage medium, or the like. More specifically, the present invention is applicable to a system including a plurality of devices or an apparatus including a single device.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-085896, filed Apr. 4, 2012, which is hereby incorporated by reference herein in its entirety.

What is claimed is:

1. An image processing apparatus comprising:
an acquisition unit configured to acquire a tomographic image of an eye to be examined; and
a quantification unit configured to quantify a degree of breakage in a photoreceptor layer in the tomographic image.

2. The apparatus according to claim 1, wherein said quantification unit obtains a value concerning at least one of a variation in a depth-direction position of the photoreceptor layer in the tomographic image and an intermittence of the photoreceptor layer.

3. The apparatus according to claim 1, wherein said quantification unit quantifies the degree of breakage in the photoreceptor layer based on a parallelness of a layer structure in the tomographic image.

4. The apparatus according to claim 1, wherein said quantification unit quantifies the degree of breakage in the photoreceptor layer based on a result of fractal analysis of the tomographic image.

5. The apparatus according to claim 1, wherein said quantification unit quantifies the degree of breakage in the photoreceptor layer based on a statistical feature of a texture of the tomographic image.

6. The apparatus according to claim 1, wherein said quantification unit calculates the tomographic image by a texture feature amount using a run-length matrix.

7. The apparatus according to claim 1, further comprising a determination unit configured to determine a region to be processed from the tomographic image,
wherein said quantification unit quantifies the degree of breakage in the photoreceptor layer of the tomographic image within the region determined by said determination unit.

8. The apparatus according to claim 7, wherein said determination unit determines the region at a position including a photoreceptor inner/outer segment near a fovea.

9. The apparatus according to claim 7, wherein said determination unit determines a depth-direction position of the region by detecting a retinal pigment epithelium from the tomographic image, and determines a tilt of the region along the retinal pigment epithelium, thereby determining the region such that the region includes the photoreceptor layer.

10. The apparatus according to claim 7, further comprising an input unit configured to accept a user operation to modify or designate a position of the region determined by said determination unit.

11. The apparatus according to claim 7, further comprising a shape correction unit configured to curve a shape of the region determined by said determination unit in accordance with a degree of a curve of a layer shape in the tomographic image.

12. The apparatus according to claim 1, further comprising a reduction unit configured to reduce speckle noise in the tomographic image acquired by said acquisition unit,
wherein said quantification unit quantifies the degree of breakage in the photoreceptor layer of the tomographic image in which the speckle noise is reduced by said reduction unit.

13. The apparatus according to claim 1, further comprising an adjustment unit configured to adjust a depth-direction pixel resolution of the tomographic image acquired by said acquisition unit,
wherein said quantification unit quantifies the degree of breakage in the photoreceptor layer of the tomographic image in which the pixel resolution is adjusted by said adjustment unit.

14. The apparatus according to claim 13, wherein said adjustment unit makes the depth-direction pixel resolution near a fovea higher than in a remaining portion.

15. The apparatus according to claim 1, further comprising a display control unit configured to cause a display unit to display a value quantified by said quantification unit.

16. The apparatus according to claim 15, further comprising a generation unit configured to generate an index of a degree of breakage in a layer structure quantified by said quantification unit,
wherein said display control unit causes the display unit to display the tomographic image and the index.

17. The apparatus according to claim 15, wherein said display control unit causes the display unit to identifiably display a region processed by said quantification unit in a superimposed manner.

18. The apparatus according to claim 1, further comprising a shape correction unit configured to perform correction to reduce a degree of a curve of a layer shape in the tomographic image.

19. The apparatus according to claim 1, further comprising:
a detection unit configured to detect a retinal pigment epithelium in the tomographic image; and
a determination unit configured to determine a region including the retinal pigment epithelium in the tomographic image as a region including the photoreceptor layer,
wherein said quantification unit quantifies a degree of breakage in a layer included in the region as the degree of breakage in the photoreceptor layer.

20. An image processing apparatus comprising:
an acquisition unit configured to acquire a tomographic image of an eye to be examined;
a detection unit configured to detect a retinal pigment epithelium in the tomographic image;
a determination unit configured to determine a region including the retinal pigment epithelium in the tomographic image; and
a quantification unit configured to quantify a degree of breakage of a layer included in the determined region.

21. The apparatus according to claim 20, wherein said determination unit determines the region in the tomographic image as a region including a photoreceptor layer of the eye, and
wherein said quantification unit obtains a value concerning at least one of a variation in a depth-direction position of the photoreceptor layer in the tomographic image and an intermittence of the photoreceptor layer.

22. The apparatus according to claim 20, wherein said quantification unit obtains a value concerning at least one of a variation in a depth-direction position of the layer in the tomographic image and an intermittence of the layer.

23. An image processing comprising steps of: acquiring, by an acquisition unit, a tomographic image of an eye to be examined; and quantifying a degree of breakage in a photoreceptor layer in the tomographic image.

24. The method according to claim 23, wherein in the step of quantifying, a value concerning at least one of a variation in a depth-direction position of the photoreceptor layer in the tomographic image and an intermittence of the photoreceptor layer is obtained.

25. The method according to claim 23, further comprising a step of determining a region to be processed from the tomographic image,
wherein in the step of quantifying, the degree of breakage in the photoreceptor layer of the tomographic image within the determined region is quantified.

26. The method according to claim 23, further comprising steps of:
detecting a retinal pigment epithelium in the tomographic image; and
determining a region including the retinal pigment epithelium in the tomographic image as a region including the photoreceptor layer,
wherein in the step of quantifying, a degree of breakage in a layer included in the region is quantified as the degree of breakage in the photoreceptor layer.

27. A non-transitory computer readable storage medium storing a program that causes a computer to execute each step of an image processing method defined in claim 23.

28. An image processing method comprising steps of:
acquiring a tomographic image of an eye to be examined;
detecting a retinal pigment epithelium in the tomographic image;
determining a region including the retinal pigment epithelium in the tomographic image; and
quantifying a degree of breakage of a layer included in the determined region.

29. The method according to claim 28, wherein in the step of determining, the region in the tomographic image is determined as a region including a photoreceptor layer of the eye, and
wherein in the step of quantifying, a value concerning at least one of a variation in a depth-direction position of the photoreceptor layer in the tomographic image and an intermittence of the photoreceptor layer is obtained.

30. A non-transitory computer readable storage medium storing a program that causes a computer to execute each step of an image processing method defined in claim 28.

31. The method according to claim 28, wherein in the step of quantifying, a value concerning at least one of a variation in a depth-direction position of the layer in the tomographic image and an intermittence of the layer is obtained.

32. An image processing apparatus comprising:
an acquisition unit configured to acquire a tomographic image of an eye to be examined;
a detection unit configured to detect a retinal pigment epithelium layer in the tomographic image;
a determination unit configured to determine a region including a photoreceptor layer in the tomographic image based on the detected retinal pigment epithelium layer; and
a quantification unit configured to quantify a degree of breakage of the photoreceptor layer.

33. The apparatus according to claim 32, wherein said quantification unit obtains a value concerning at least one of a variation in a depth-direction position of the photoreceptor layer in the tomographic image and an intermittence of the photoreceptor layer.

34. An image processing method comprising:
acquiring a tomographic image of an eye to be examined;
detecting a retinal pigment epithelium layer in the tomographic image;
determining a region including a photoreceptor layer in the tomographic image based on the detected retinal pigment epithelium layer; and
quantifying a degree of breakage of the photoreceptor layer.

35. The method according to claim 34, wherein in the step of quantifying, a value concerning at least one of a variation in a depth-direction position of the photoreceptor layer in the tomographic image and an intermittence of the photoreceptor layer is obtained.

36. A non-transitory computer-readable storage medium storing a program for causing a computer to execute a method, the method comprising:
acquiring a tomographic image of an eye to be examined;

detecting a retinal pigment epithelium layer in the tomographic image;

determining a region including a photoreceptor layer in the tomographic image based on the detected retinal pigment epithelium layer; and quantifying a degree of breakage of the photoreceptor layer.

* * * * *